(12) United States Patent
Rivier

(10) Patent No.: US 12,390,594 B2
(45) Date of Patent: Aug. 19, 2025

(54) GLASS LUER TIP WITH MARKING AND METHOD FOR MANUFACTURING THE SAME

(71) Applicant: Becton Dickinson France, Le Pont de Claix (FR)

(72) Inventor: Cédric Rivier, Voreppe (FR)

(73) Assignee: Becton Dickinson France, Le Pont de Claix (FR)

( * ) Notice: Subject to any disclaimer, the term of this patent is extended or adjusted under 35 U.S.C. 154(b) by 991 days.

(21) Appl. No.: 17/259,300

(22) PCT Filed: Jul. 2, 2019

(86) PCT No.: PCT/EP2019/067744
§ 371 (c)(1),
(2) Date: Jan. 11, 2021

(87) PCT Pub. No.: WO2020/011603
PCT Pub. Date: Jan. 16, 2020

(65) Prior Publication Data
US 2021/0252225 A1 Aug. 19, 2021

(30) Foreign Application Priority Data
Jul. 12, 2018 (EP) ..................................... 18305940

(51) Int. Cl.
*A61M 39/10* (2006.01)
*A61M 5/31* (2006.01)
*C03B 25/00* (2006.01)
*C03C 15/00* (2006.01)
*C03C 17/22* (2006.01)

(52) U.S. Cl.
CPC .......... *A61M 5/3134* (2013.01); *A61M 39/10* (2013.01); *C03B 25/00* (2013.01); *C03C 15/00* (2013.01); *C03C 17/22* (2013.01); *A61M 2039/1044* (2013.01); *A61M 2039/1083* (2013.01); *A61M 2205/0211* (2013.01); *A61M 2205/582* (2013.01); *A61M 2205/583* (2013.01); *A61M 2207/00* (2013.01)

(58) Field of Classification Search
None
See application file for complete search history.

(56) References Cited

U.S. PATENT DOCUMENTS

| | | | | | |
|---|---|---|---|---|---|
| 2,073,067 | A | * | 3/1937 | Klein | .................... A61M 5/347 |
| | | | | | 215/12.2 |
| 3,032,433 | A | * | 5/1962 | Lewis | .................... B05B 12/24 |
| | | | | | 156/247 |

(Continued)

FOREIGN PATENT DOCUMENTS

| | | |
|---|---|---|
| CN | 101756785 A | 6/2010 |
| CN | 105102055 A | 11/2015 |

(Continued)

*Primary Examiner* — Jodi C Franklin
(74) *Attorney, Agent, or Firm* — The Webb Law Firm

(57) ABSTRACT

The present invention relates to a glass luer tip with marking means for completing a leak-free luer slip connection with a female fitting. The invention also relates to a method for manufacturing such a marked glass luer tip. The method further relates to the use of such a marked glass luer tip for completing a leak-free luer slip connection.

12 Claims, 1 Drawing Sheet

(56) References Cited

U.S. PATENT DOCUMENTS

| | | | |
|---|---|---|---|
| 3,402,713 A * | 9/1968 | Senkowski | F16L 15/006 |
| | | | 264/318 |
| 4,312,344 A * | 1/1982 | Nilson | A61M 5/2425 |
| | | | 604/232 |
| 4,529,095 A * | 7/1985 | Hansen | B65D 23/00 |
| | | | 215/331 |
| 4,589,871 A * | 5/1986 | Imbert | A61M 5/346 |
| | | | 29/402.18 |
| 5,147,329 A * | 9/1992 | Brannon | A61B 5/150236 |
| | | | 604/231 |
| 5,591,143 A | 1/1997 | Trombley, III et al. | |
| 5,851,201 A * | 12/1998 | Ritger | A61M 39/10 |
| | | | 604/533 |
| 6,013,037 A * | 1/2000 | Brannon | A61B 5/150496 |
| | | | 600/576 |
| 6,090,386 A * | 7/2000 | Griffith | C07K 14/415 |
| | | | 530/324 |
| 6,189,292 B1 * | 2/2001 | Odell | B65B 3/003 |
| | | | 53/425 |
| 6,651,405 B1 * | 11/2003 | Vetter | B23P 19/00 |
| | | | 53/309 |
| 6,969,375 B2 * | 11/2005 | Thibault | A61M 5/344 |
| | | | 604/241 |
| 7,036,288 B2 * | 5/2006 | Vetter | B65B 3/003 |
| | | | 53/493 |
| 7,195,606 B2 * | 3/2007 | Ballin | A61B 5/150221 |
| | | | 604/6.02 |
| 8,105,312 B2 * | 1/2012 | Uematsu | A61M 39/02 |
| | | | 604/533 |
| 9,017,291 B2 | 4/2015 | Delabie | |
| 9,579,497 B2 * | 2/2017 | Cude | A61M 39/10 |
| 9,861,555 B2 * | 1/2018 | Tennican | A61J 1/2096 |
| 2004/0210196 A1 | 10/2004 | Bush, Jr. et al. | |
| 2004/0220533 A1 * | 11/2004 | Caizza | A61M 5/34 |
| | | | 604/240 |
| 2005/0124980 A1 | 6/2005 | Sanders | |
| 2007/0271960 A1 * | 11/2007 | Scholz | C03B 23/097 |
| | | | 65/297 |
| 2008/0275387 A1 * | 11/2008 | Yeadon | A61M 5/284 |
| | | | 604/82 |
| 2009/0177186 A1 | 7/2009 | Delano | |
| 2010/0280462 A1 | 11/2010 | Kommireddy et al. | |
| 2012/0179108 A1 | 7/2012 | Delabie | |
| 2013/0046174 A1 * | 2/2013 | Fischell | A61B 90/39 |
| | | | 600/431 |
| 2013/0221288 A1 * | 8/2013 | Liu | H05K 1/097 |
| | | | 977/932 |
| 2014/0039413 A1 | 2/2014 | Jugl et al. | |
| 2014/0350477 A1 | 11/2014 | Lee | |
| 2015/0157811 A1 * | 6/2015 | Zuidema | A61M 5/34 |
| | | | 285/8 |
| 2016/0199569 A1 | 7/2016 | Yevmenenko et al. | |
| 2016/0243584 A1 * | 8/2016 | Hayashi | B05D 1/002 |
| 2016/0318789 A1 * | 11/2016 | Gromann | C03B 23/045 |
| 2016/0324455 A1 * | 11/2016 | Crosby | A61B 5/150022 |
| 2017/0224975 A1 * | 8/2017 | Peer | A61M 39/10 |
| 2018/0028801 A1 | 2/2018 | Jin et al. | |
| 2018/0085568 A1 * | 3/2018 | Drmanovic | A61M 5/3134 |
| 2019/0217019 A1 * | 7/2019 | Kondo | A61M 5/28 |
| 2019/0381258 A1 * | 12/2019 | Doubet | A61M 5/34 |
| 2020/0121864 A1 | 4/2020 | Brunel et al. | |
| 2020/0405978 A1 * | 12/2020 | Doubet | B29C 45/261 |

FOREIGN PATENT DOCUMENTS

| | | | | |
|---|---|---|---|---|
| DE | 10340708 A1 | | 3/2005 | |
| DE | 102011079078 A1 * | | 1/2013 | B29C 49/4205 |
| EP | 1473053 A1 * | | 11/2004 | A61M 5/3216 |
| EP | 2514461 A1 | | 10/2012 | |
| GB | 2341805 A * | | 3/2000 | A61M 5/322 |
| JP | 2005169113 A | | 6/2005 | |
| JP | 2012530586 A | | 12/2012 | |
| RU | 2355431 C2 * | | 5/2009 | A61M 5/32 |
| WO | WO-0191839 A1 * | | 12/2001 | A61M 5/344 |
| WO | WO-2005019360 A1 * | | 3/2005 | B41J 11/0015 |
| WO | 2018122366 A1 | | 7/2018 | |

* cited by examiner

GLASS LUER TIP WITH MARKING AND METHOD FOR MANUFACTURING THE SAME

CROSS-REFERENCE TO RELATED APPLICATIONS

This application is the United States national phase of International Application No. PCT/EP2019/067744 filed Jul. 2, 2019, and claims priority to European Patent Application No. 18305940.1 filed Jul. 12, 2018, the disclosures of which are hereby incorporated by reference in their entirety.

BACKGROUND OF THE INVENTION

Field of the Invention

The present invention relates to a glass made luer tip for an injection device, the luer tip having marking means for indicating to a user where to position a proximal end of a female fitting intended to be connected to the luer tip, in order to obtain a leak-free connection. The invention also relates to a method for manufacturing such a luer tip. The invention further relates to the use of such a marked luer tip and to a method using such a marked luer tip for completing a leak-free luer slip connection with a female fitting. The invention also relates to an injection device comprising such a marked luer tip.

In the present application, the distal end of a piece or a device is understood to be the end furthest from the hand of the user and the proximal end is understood to be the end closest to the hand of the user. Likewise, in the present application, "distal direction" is understood to be the direction of injection, with reference to an injection device, and "proximal direction" is understood to be the direction opposite the direction of injection.

DESCRIPTION OF RELATED ART

In the field of injection devices, it happens that the needle may not be part of the injection device itself and needs to be connected to a tip of the injection device at the time the user is ready to proceed to the injection. This is the case in particular when the tip of the injection device is made of glass. In such a case, a separate needle, also called a detached needle, is provided to be connected to the tip of the injection device. Various connections systems are available for connecting the needle to the tip of the injection device.

One of the available connections is the luer slip connection. Such a connection is intended to provide a connection between injection devices, such as glass hypodermic syringes for example, and needles. In the present application, by "luer slip connection" is meant a friction fit connection between a frustoconical male luer tip and a corresponding hollow conical female fitting.

In response to the need to create safer standard medical connections, standards have been set up regarding the dimensions of the elements forming a connection. ISO 80369-7 is a standard giving the dimensions of the elements of a luer slip connection. By standardized dimensions, is meant according to the present document dimensions in conformity with ISO 80369-7.

According to these standards, the tip of the injection device is formed of a luer which is a conical tip having a 6% taper, also called male part of the connection. The female part of the connection, hereinafter called the female fitting, is a needle hub or other luer connection having a conical hollow connecting part provided with an inner surface intended to match the 6% taper of the luer tip. The luer slip connection is a friction-fit connection that requires the user to insert the luer tip of the injection device into the female fitting in a push-and-twist manner.

The push-and-twist manner to complete the connection is supposed to ensure a connection that is less likely to detach. Simply sliding the female fitting onto the luer tip of the injection device may not ensure a secure fitting.

Actually, luer slip connection is often used when the tip of the injection device is made of glass. Anyway, despite the standardized dimensions of the tip of the injection device and of the female fitting, it may happen that the connection is neither totally correct nor safe, because of the relatively high dimensional tolerances, compared to plastic syringes, which are inherent to glass made pieces.

For example, the needle may detach from the tip and be ejected therefrom during injection of viscous drug if the needle is not safely connected to the tip. Moreover, if the female fitting is not sufficiently pushed for example, leaks of product may occur and the injection step may be compromised.

The female fitting should therefore be correctly positioned at the end of the push-and-twist step.

But connecting glass injection devices and needles actually raises other issues. Indeed, for each injection device, the connection between the glass luer tip and the female fitting, such as a needle hub or other connecting device, is dependent not only on the dimensional tolerances specific to said glass luer tip but also on the human being performing the connection, in other words, the user. Each user will insert the luer tip into the female fitting with a unique force, according to a unique direction, and according to a unique gesture, in particular a push-and-twist gesture. As a consequence, the connection is not reproducible. In addition, each user may have a different sense of what a correct connection is and how a correct connection is performed.

As a result, depending on the dimensional tolerances of the glass luer tip and depending on the user completing the connection, it may happen that, for some connections, the distal end of the luer tip either does not reach the distal end of the hollow cone forming the female fitting and/or is not positioned at the correct place in the axial direction.

As already mentioned, leaks of product may result from such a situation and the injection step may be compromised. In addition, the needle may detach from the luer tip during the injection.

Document WO2018/122366 shows a luer tip the outer surface of which is provided with ribs. Anyway, there is no indication in this document where exactly these ribs are positioned on the luer tip.

There is therefore the need for a tip and/or a method that would allow a user to complete a leak-free connection between a luer tip and a female fitting it is intended to be connected to, in the case of a luer slip connection.

SUMMARY OF THE INVENTION

A first aspect of the invention is a glass made male luer tip for an injection device, intended to be connected to a female fitting via a luer slip connection, wherein said male luer tip comprises marking means configured to indicate to a user where to position a proximal end of said female fitting for completing a leak-free connection. More particularly, an aspect of the invention is a glass made frustoconical male luer tip for an injection device, intended to be connected to a corresponding hollow conical female fitting via a friction fit connection, wherein said male luer tip comprises marking means configured to indicate to a user where to position a proximal end of said female fitting for completing a leak-free connection.

In particular, the marking means are configured to indicate to the user where to position the proximal end of the female fitting with respect to said tip in order to complete a leak-free connection between said tip and said female fitting. For example, the marking means are disposed on a very specific place, particularly on an outer surface of the male luer tip, in order to indicate to the user where to position the female fitting, in order to complete a leak-free connection.

Another aspect of the invention is a method for manufacturing a glass made male luer tip for an injection device, provided with marking means configured to indicate to a user where to position a proximal end of a female fitting for completing a leak-free luer slip connection with said tip, said method comprising the following steps:
  A) preforming the tip from glass,
  B) annealing said preformed tip,
  C) Applying onto the tip a gage having standardized dimensions so as to determine on the tip the location where to position said marking means, and
  D) Providing said tip with said marking means at said location, wherein step B) may take place either before step C) or after step D).

In other words, an aspect of the invention is a method for manufacturing a glass made frustoconical male luer tip for an injection device, provided with marking means configured to indicate to a user where to position a proximal end of a corresponding hollow conical female fitting for completing a leak-free friction fit connection with said tip, said method comprising the following steps:
  A) preforming the tip from glass,
  B) annealing said preformed tip,
  C) Applying onto the tip a gage having standardized dimensions so as to determine on the tip the location where to position said marking means, and
  D) Providing said tip with said marking means at said location, wherein step B) may take place either before step C) or after step D).

Another aspect of the invention is the use of the glass made male luer tip as above or of the glass made luer tip obtained by the method above for completing a leak-free luer slip connection with a female fitting. In other words, another aspect of the invention is the use of the glass made frustoconical luer tip as above or of the glass made frustoconical luer tip obtained by the method above for completing a leak-free friction fit connection with a corresponding hollow conical female fitting.

Another aspect of the invention is a method for completing a leak-free luer slip connection between the glass made male luer tip as above or obtained by the manufacturing method above and a female fitting, said method comprising the step of pushing and twisting said female fitting onto said male luer tip until a proximal end of said female fitting reaches said marking means. In other words, another aspect of the invention is a method for completing a leak-free friction fit connection between the glass made frustoconical male luer tip as above or the glass made frustoconical luer tip obtained by the method above and a corresponding hollow conical female fitting, said method comprising the step of pushing and twisting said female fitting onto said male luer tip until a proximal end of said female fitting reaches said marking means.

Another aspect of the present invention is an injection device comprising the glass made luer tip as above or obtained by the manufacturing method above.

The marked glass made luer tip of the invention and the method of the invention allow performing a secure and leak-free luer slip connection between said glass made luer tip and a female fitting it is intended to be connected to, such as a needle hub or other luer connection. Thanks to the marked glass made luer tip of the invention and to the method of the invention, the user may feel confident that the connection he performs will be safe and secured, for each new connection to performed, from one injection device needed to be connected to a needle to another. Indeed, thanks to the luer tip and the method of the invention, the user may have this comforting feeling, independently from the fact that the luer tip, due to its glassy nature submitted to dimensional tolerances, may vary in dimensions from one luer tip to another. The user may also have this comforting feeling, independently from the fact that he, as a human being, may apply variations, intentionally or not, from one gesture to another, each time he performs such a connection.

In embodiments, the marking means may be selected from a visual indicator, a tactile indicator and/or combinations thereof, located on a surface of said tip. The user may therefore either look at the indicator or feel it with a finger for example. The marking means may have an annular shape. Such embodiments allow the user to see or feel the presence of the marking means more easily. For example, the marking means is selected from a print, an engraving, a relief and combinations thereof. In embodiments, the marking means is an annular print.

The method for manufacturing the marked glass made male luer tip above comprises the following steps:
  A) preforming the tip from glass,
  B) annealing said preformed tip,
  C) Applying onto the tip a gage having standardized dimensions so as to determine on the tip the location where to position said marking means, and
  D) Providing said tip with said marking means at said location,
  wherein step B) may take place either before step C) or after step D).

In the present document, by "gage having standardized dimensions", it is meant a gage having the dimensions as set forth in ISO 80369-7.

In a first step, step A), for manufacturing the marked luer tip of the invention, the tip is preformed from glass. The tip may be formed on its own or may be preformed together with the barrel of a glass injection device as a single piece. This preforming step is completed according to glass forming methods known in the art.

In a first embodiment of the manufacturing method of the invention, the preformed tip obtained at step A) is annealed before applying any marking means.

In such a first embodiment, the preformed tip is therefore annealed according to a second step, step B) of the method. The annealing step may be performed at a temperature ranging from about 200° C. to about 800° C.

Once the annealed preformed tip has cooled down, a gage having standardized dimensions is applied onto the tip in a third step, step C). This step allows determining on the tip, in particular on an outer surface of the tip, the location where to position the markings means. In embodiments, the gage is a physical gage. For example, the gage may be a stainless steel gage applied onto said tip by axial force. In other embodiments, the gage is a virtual gage applied to the tip by a camera.

Step C) above allows determining the location where to position the marking means for each individual glass luer tip to be marked, regardless from the fact that the dimensions of glass luer tips may vary from one glass luer tip to another, due to dimensional tolerances inherent to glass products. The dimensional variations of the glass luer tips have therefore no impact on the correctness of the location determined for one individual glass luer tip, thanks to the use of a gage in conformity with step C).

Once the location where to position the marking means is determined for the glass luer tip, said marking means are provided at said location according to a fourth step, step D). Step D) may comprise ink printing said tip and/or laser printing said tip. For example, an annular print is printed at the determined location on the outer surface of the tip. Alternatively, an engraving is performed at the determined location on the outer surface of the tip by laser printing. The engraving may form a relief on the surface of the tip.

A marked glass luer tip is obtained, that may be used for connecting securely a female fitting to the injection device via a luer slip connection.

In an alternative embodiment of the manufacturing method of the invention, the marking means are applied to the preformed tip obtained at step A) before the annealing step.

In the case of such a second embodiment, step C) is performed after step A) and the gage having standardized dimensions is applied onto the preformed glass tip. Like above, the gage may be a physical gage, such as a stainless steel gage that may be applied onto the tip by axial force, or alternatively a virtual gage applied to the preformed glass tip by a camera. Like in the first embodiment, this step allows determining on the tip, in particular on an outer surface of the tip, the location where to position the markings means.

Like above, this step allows determining the location where to position the marking means for each individual glass luer tip to be marked, regardless from the fact that the dimensions of glass luer tips may vary from one glass luer tip to another, due to dimensional tolerances inherent to glass products. The dimensional variations of the glass luer tips have therefore no impact on the correctness of the location determined for one individual glass luer tip, thanks to the use of a gage.

In such a second embodiment of the manufacturing method of the invention, the marking means are provided at said location according to a fourth step, step D), which may comprise enamel printing said tip and/or glass relief forming on said tip.

For example, enamel is deposited as an annular band at the determined location on the surface of the tip. Alternatively, a relief, such as a groove or a ridge, for example an annular groove or an annular ridge, may be formed by glass forming at the location determined by the gage at the preceding step.

In a next step, annealing step B), the glass luer tip, provided with the marking means, such as an enamel deposit or a glass relief, is annealed. The annealing step may be performed at a temperature ranging from about 200° C. to about 800° C. Such an annealing step allows fixing the shape of the marked tip.

A marked glass luer tip is obtained, that may be used for connecting securely a female fitting to the injection device via a luer slip connection.

The manufacturing method of the invention, regardless form the first or second embodiment described above, may further comprise a step of depositing a ceramic coating onto said tip. This ceramic coating step may take place before the annealing step B). The ceramic coating allows providing additional roughness onto the surface of the glass luer tip, thereby ensuring an improved friction fit when the female fitting is connected onto the glass luer tip.

The marked glass luer tip as above may be used for completing a leak-free luer slip connection with a female fitting. For example, such a leak-free luer slip connection may be completed by pushing and twisting a female fitting onto the marked glass luer tip of the invention until a proximal end of the female fitting reaches the marking means of the marked glass luer tip. When the proximal end of the female fitting reaches the marking means, such as an annular print, the user knows that the female fitting is correctly positioned axially with respect to the glass luer tip, and the connection is safe and leak-free.

The marked glass luer tip of the invention may be part of an injection device, such as a glass syringe.

BRIEF DESCRIPTION OF THE DRAWINGS

The invention will now be described in details, with reference to the enclosed drawings in which.

DETAILED DESCRIPTION OF THE INVENTION

Figure 1:
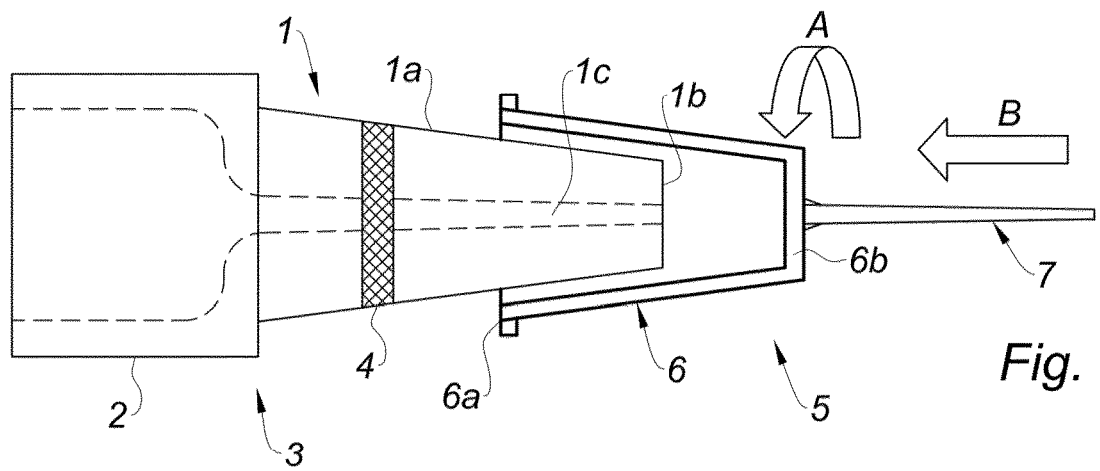
FIG. 1 is a side schematic view of a marked glass luer tip of the invention onto which a female fitting is in the process of being connected.

With reference to FIG. 1, is shown partially and schematically a glass made male luer tip 1 of the invention positioned at a distal end of the glass barrel 2 of an injection device 3. The tip 1 is provided with a channel 1c (shown in dotted line) for the passage and delivery of the product (not shown) contained in the glass barrel 2.

The glass luer tip 1 has the shape of a 6% taper cone in conformity with ISO 80369-7. It is provided with a marking means, under the shape of an annular print 4 located on the outer surface 1a of the glass luer tip 1. The glass luer tip 1 has a distal end 1b.

With reference to FIG. 1 is also shown a needle hub 5. The needle hub 5 comprises a hollow 6% taper cone, under the form of a female fitting 6, intended to be connected onto the glass luer tip 1. The female fitting 6 comprises a proximal end 6a and a distal end 6b where a needle 7 is provided.

The female fitting 6 is intended to be connected to the glass luer tip 1 via a luer slip connection: according to such a connection, the female fitting 6 is mounted onto the glass luer tip 1 in a push-and-twist manner in conformity with the arrows A and B shown on FIG. 1.

The marking means, such as the annular print 4, is configured to indicate to a user where to position the proximal end 6a of the female fitting 6 for completing a leak-free connection. The marking means constitute a visual indicator of such a position. In embodiments not shown, the marking means could be under the form of a tactile indicator.

For example, the marking means could be under the form of an engraving and/or a relief.

Figure 2:
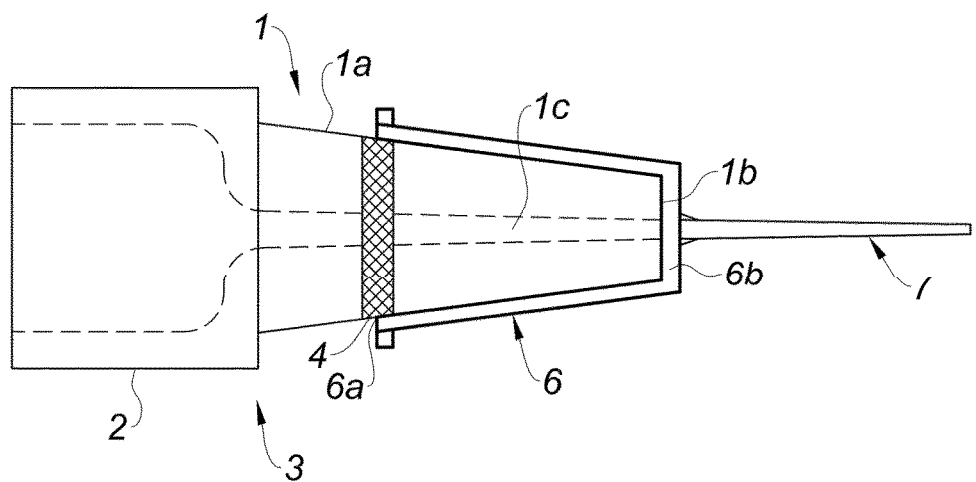
FIG. 2 is a side schematic view of the marked glass luer tip and the female fitting of FIG. 1 once the secured connection is completed.

With reference to FIG. 2, the glass luer tip 1 and the female fitting 6 of FIG. 1 are shown once the luer slip connection is completed. As shown in this FIG., the proximal end 6a of the female fitting is positioned at the location of the annular print 4. It can be observed that in such a position of the proximal end 6a of the female fitting 6 with respect to the annular print 4, the distal end 1b of the glass luer tip 1 is in contact with the wall of the distal end 6b of the female fitting 6. The connection between the glass luer tip 1 and the female fitting 6 is therefore secure and leak-free.

The user can feel comfortable with the fact that the connection is safe and the needle will not detach during the injection step.

Figure 3:
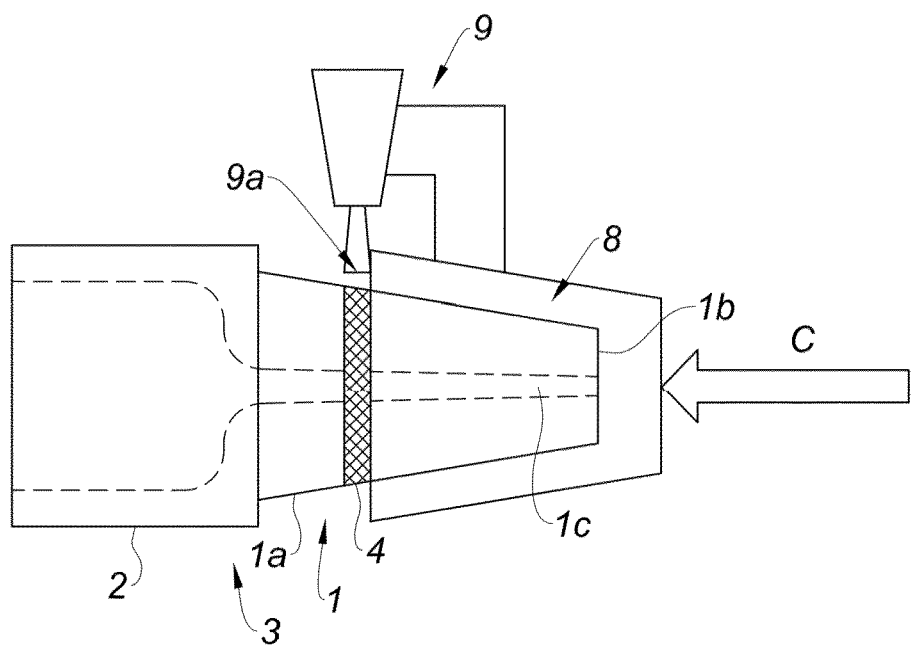
FIG. 3 is a schematic side view of the step of applying the marking means onto a glass luer tip according to the manufacturing method of the invention.

With reference to FIG. 3 is shown a step of the method of the invention for manufacturing the marked glass luer tip 1 of FIGS. 1 and 2.

According to this method, in a first step (not shown), the barrel and the tip of an injection device are preformed from glass. Alternatively, the tip may be preformed from glass on its own. This preforming step is completed according to well-known glass forming methods.

The preformed tip is then annealed. For example, the annealing step may be performed at a temperature ranging from about 200° C. to about 800° C.

The annealing step may also include a step of depositing a ceramic coating onto the tip, before annealing as such. The ceramic coating allows providing additional roughness onto the surface of the glass luer tip, once the coated tip is annealed. The presence of a ceramic coating on the tip allows an improved friction fit when the female fitting is connected onto the glass luer tip later on.

With reference to FIG. 3, once the annealed preformed tip 1 has cooled down, a gage 8 having standardized dimensions in conformity with ISO 80369-7 is applied onto the tip 1. The gage 8 may be a physical gage, such as a stainless steel gage that may be applied onto the tip 1 by axial force according to the arrow C shown on FIG. 3. Alternatively, the gage may be a virtual gage applied to the preformed glass tip 1 by a camera.

Application of the gage 8 onto the tip 1 allows determining the location where to position the marking means, such as the annular print 4, for each individual glass luer tip 1 to be marked, regardless from the fact that the dimensions of glass luer tips vary from one glass luer tip to another, due to dimensional tolerances inherent to glass products. The dimensional variations of the glass luer tips have therefore no impact on the correctness of the location determined for one individual glass luer tip 1, thanks to the use of a gage in the method of the invention.

Once the location where to position the marking means is determined for the glass luer tip, the marking means are provided at said location.

With reference to FIG. 3, for example, an annular print 4 is applied thanks to a printer 9 provided with a nozzle 9a for delivering printing ink.

In embodiments not shown, the marking means could be an engraving provided at the determined location by means of laser printing.

In alternative embodiments of the method of the invention, the marking means could be applied onto the glass luer tip before the annealing step. This is the case for example when the marking means are selected from enamel printing and/or glass relief forming the tip. For example, enamel is deposited as an annular band at the determined location on the surface of the tip. Alternatively, a relief, such as a groove or a ridge, for example an annular groove or an annular ridge, is formed by glass forming at the location determined by the gage at the preceding step.

The marked glass luer tip is then annealed in order to fix either the enamel printing or the shape of the relief obtained by glass forming.

The marked glass luer tip 1 is obtained, that may be used for connecting securely a female fitting 6 to the injection device via a luer slip connection as described in relation with FIGS. 1 and 2.

The marked glass made luer tip of the invention and the method of the invention allow performing a secure and leak-free luer slip connection between said glass made luer tip and a female fitting it is intended to be connected to, such as a needle hub or other luer connection. For each new connection, said connection is safe, independently from the variations of the dimensions of the glass luer tip and independently from the variations of the gesture completed by the human being performing the connection.

The invention claimed is:

1. A method for manufacturing a glass frustoconical male luer tip for an injection device, said method comprising the following steps:
   (A) preforming the tip from glass;
   (B) annealing said preformed tip;
   (C) applying onto the tip a gage comprising a hollow tapered cone having a proximal end with an opening configured to receive the tip and a distal end opposite the proximal end, the tapered cone having standardized dimensions corresponding to a location on the tip where to position a marking indicating where to position a proximal end of a corresponding hollow conical female fitting for completing a leak-free friction fit connection with said tip; and
   (D) providing said tip with said marking external to and adjacent the proximal end of the gage;
   wherein step (B) may take place either before step (C) or after step (D).

2. The method according to claim 1, wherein said gage is a physical gage.

3. The method according to claim 1, wherein when step (B) takes place before step (C), step (D) comprises ink printing said tip and/or laser printing said tip.

4. The method according to claim 1, wherein when step (B) takes place after step (D), step (D) comprises enamel printing said tip and/or glass relief forming on said tip.

5. The method according to claim 1, further comprising a step of depositing a ceramic coating onto said tip taking place before step (B).

6. The method according to claim 1, further comprising completing a leak-free friction fit connection with said tip and a corresponding hollow conical female fitting.

7. The method according to claim 1, further comprising a step of pushing and twisting said female fitting onto said male luer tip until a proximal end of said female fitting reaches said marking.

8. The method according to claim 1, wherein the standardized dimensions are in conformity with ISO 80369-7.

9. The method according to claim 1, wherein step (B) takes place before step (C).

10. The method according to claim 1, wherein step (B) takes place after step (D).

11. The method according to claim 2, wherein said physical gage is a stainless steel gage applied onto said tip by axial force.

12. A method for completing a leak-free friction fit connection between said glass frustoconical male luer tip obtained by the method of claim 1 and a corresponding hollow conical female fitting, said method comprising a step of pushing and twisting said female fitting onto said male luer tip until a proximal end of said female fitting reaches said marking.

* * * * *